Figure 1:
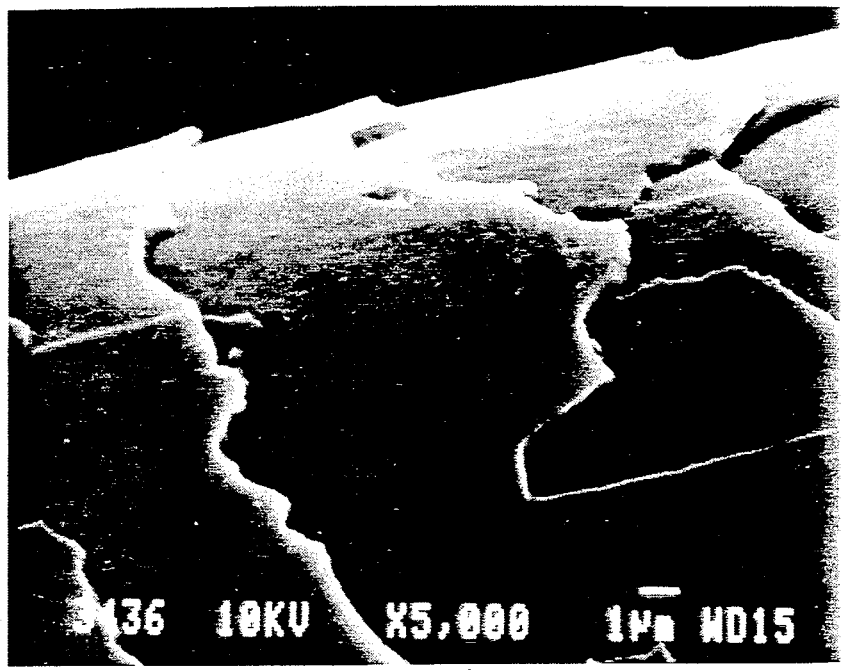

United States Patent [19]

Jachowicz et al.

[11] Patent Number: 5,147,635
[45] Date of Patent: Sep. 15, 1992

[54] CONDITIONERS BASED ON CATIONIC POLYMERS

[75] Inventors: Janusz Jachowicz, Bethel, Conn.; Chittamura Ramireddy, Austin, Tex.

[73] Assignee: Clairol Incorporated, New York, N.Y.

[21] Appl. No.: 770,195

[22] Filed: Oct. 2, 1991

Related U.S. Application Data

[62] Division of Ser. No. 481,417, Feb. 16, 1990.

[51] Int. Cl.$^5$ .................. A61K 7/075; A61K 7/08
[52] U.S. Cl. ........................... 424/72; 424/70; 424/71
[58] Field of Search .............. 424/70, 71, 72; 520/240, 287, 242, 301, 302

[56] References Cited

U.S. PATENT DOCUMENTS

| | | | |
|---|---|---|---|
| 3,408,338 | 10/1968 | Szita et al. | 576/302 X |
| 3,412,077 | 11/1968 | Szita et al. | 576/302 X |
| 4,454,114 | 6/1984 | Strasilla et al. | 424/70 |

*Primary Examiner*—Joseph L. Schofer
*Assistant Examiner*—Nagumo M.
*Attorney, Agent, or Firm*—Anthony M. Santini

[57] ABSTRACT

A composition for treating keratinaceous substrates which contains a cationic polymer having units of formula I:

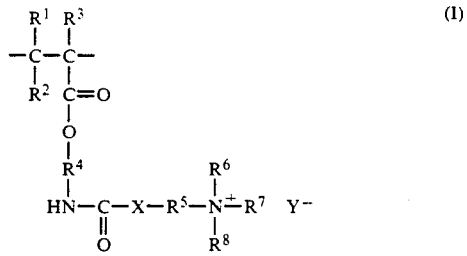

wherein:
(a) $R^1$, $R^2$ and $R^3$ are each independently selected from the group consisting of H, halogen, alkyl, $C_{1-6}$ alkoxy, $C_{1-6}$ aminoalkyl, $C_{1-6}$ *haloalkyl, phenyl*, $C_{1-6}$ alkylphenyl, $C_{1-6}$ alkoxyphenyl, halophenyl containing 1 to 5 halogen atoms, and aminophenyl containing 1 to 5 amino groups;
(b) $R^4$ and $R^5$ are each independently $C_{1-20}$ alkylene linkages bearing from 0 to 10 halogen or $C_{1-6}$ alkoxy substituents;
(c) X is —O— or —NH—;
(d) $R^6$, $R^7$, and $R^8$ are each independently $C_{1-20}$ alkyl, with the proviso that at least one of $R^6$, $R^7$, and $R^8$ contains a $C_{10-20}$ groups; and
(e) Y is a halide ion or $C_{1-6}$ alkyl sulfate ion;

in the presence of a non-polymeric surfactant selected from the group consisting of amphoteric surfactants, anionic surfactants and mixtures thereof.

6 Claims, 1 Drawing Sheet

CONDITIONERS BASED ON CATIONIC POLYMERS

This is a divisional application of application Ser. No. 07/481,417, filed Feb. 16, 1990.

RELATED APPLICATIONS

This application deals with subject matter which is related to the teachings of U.S. Ser. No. 07/240,787, and U.S. Pat. No. 4,818,245.

BACKGROUND

The formulation of one-step cleaning and conditioning compositions for keratinaceous substrates, e.g., human hair involves many chemical considerations. Principal among these considerations are (1) the usefulness of the composition, (2) the compatibility of the ingredients therein, and (3) the stability of the final formulation.

In formulations which employ electrolytic agents, i.e., ingredients having characteristic electronic charges, it has long been problematical to find a system in which the polarity of the molecules is sufficient to leave the substrate in an improved condition but insufficient to interfere with either the function of one or more of the cleaning or surfactant ingredient(s) or the stability of the composition.

For example, stable and homogenous compositions can usually be formulated by combining amphoteric, nonionic, and cationic surfactants with anionic detergents. Low density cationic polymers are also compatible with an excess of anionic surfactants. Such systems are, however, not very effective in conditioning hair, i.e., in improving combability. High charge density cationic polymers, which produce more pronounced conditioning effects, are incompatible with anionic detergents, and are used in combination with amphoteric or nonionic surfactants.

Compositions based on nonionic or amphoteric surfactant systems possess, however, inadequate cleansing and foaming characteristics. The compositions are also difficult to thicken.

THE INVENTION

It has been found that high charge density, cationic polyelectrolytes containing at least one of urethane and urea groups, and derived from isocyanatoethyl (meth)acrylates or (meth) acrylic acids have good conditioning properties and ca be formulated in the presence of a mixture of amphoteric and anionic surfactants. In preferred embodiments, shampoo compositions with urea- and urethane-containing polymers or copolymers produced perceptible improvements in wet combability, and showed good foamability. Surface electron microscope (SEM) examination of hair after multiple shampooings showed no excessive surface deposits of polymer-surfactant complex.

The invention deals with novel cationic polyelectrolytic materials, as well as their production, compositions containing these materials and methods of using the compositions.

Unless stated otherwise, all references cited herein are hereby incorporated by reference

DESCRIPTION OF THE PRIOR ART

In JP58/138799, entitled "Polymers as Hair Conditioners in Shampoos", described at CA 100(16): 126720m, Shiseido Co. describes shampoos which contain cationic polymers as hair conditioners. The shampoos also contain three surfactants: alkyloylalkyltaurine salt anionics, trialkylaminoacetate betaine amphoterics and alkylolamide nonionics.

U.S. Pat. No. 3,962,418 describes thickened shampoos containing anionic surfactants, zwitterionic and amphoteric surfactants, polyethoxylated nonionics, and cationic cellulosic agents as thickeners and conditioners.

U.S. Pat. No. 3,996,146 shows an acid pH shampoo which contains a cationic resin and at least two anionic detergents. The cationic resins may be copolymers of acrylamide with a quaternary ammonium substituted methacrylate U.S. Pat. No. 4,278,809 describes the production of 2-isocyanatoalkyl esters of alkenoic acids via the reaction of aqueous 2-oxazoline with phosgene in the presence of a hydrochloric acid acceptor.

U.K. Patent 1,603,321 (which has U.S. Pat. Nos. 4,240,450; 4,445,521 and 4,719,099 as counterparts) deals with the treatment of keratinaceous materials with formulations which contain polymeric anionic and cationic materials. The use of additional cationic or anionic surfactants and nonionic or amphoteric polymers and surfactants as optional ingredients is disclosed (see page 38, lines 62+).

U.S. Pat. No. 4,818,245 to J. Jachowicz et al discloses cationic polymers which may be used in hair treatment compositions.

ADVANTAGES OF THE INVENTION

The polymers, compositions and methods of the invention are components of hair care systems whose use yields several advantages over the prior art.

Shampoos and conditioners containing conventional surfactants and cationic polymers having at least one of urea-and urethane-linkages in the side chains, along with quaternary nitrogen groups do not form precipitates upon standing. It is believed that the presence of the urea and urethane linkages contributes to the solution stability and compatibility of the various electrolytic species in the formulation.

The formulations of the invention preferably contain only one type of polymeric ingredient having polar character—i.e., the novel cationic polymer(s). The absence of other polymeric molecules in the formulations appears to enhance their performance and stability characteristics, as well as such physical properties as foaminess and thickness.

The shampoos and conditioners of the invention are usable in "one-step" hair treatments. That is, one shampoo and rinse cycle is all that is needed to render the hair more manageable, especially more easily combed when wet. In addition, the formulations do not exhibit substantial build up on the hair after successive washings. This means that the dullness or plastic feel associated with the use of some conditioners is avoided.

Furthermore, the cationic polymers of the invention are high charge density molecules. Thus, they yield more effective conditioning than substances which have low charge density. In addition, the hydrophobically modified cationic copolymers of the invention, having structures IV and V as shown hereinafter, are also useful in skin care formulations. They give the skin smooth and nonsticky feel after application from aqueous or ethanol/water solution.

Treatment formulations containing the novel cationic polymers of the invention are superior in physical appearance to formulations containing various other polymeric cationics. They are usually clear liquids showing no significant cloudiness or opacity upon standing. Thus, they can be applied in atomized or other sprayable forms without fear of clogging the spraying device.

These and other advantages of the invention will be apparent after a consideration of the following description and claims.

DESCRIPTION OF THE INVENTION

Unless otherwise stated, all percentages recited herein are weight percentages based on total composition weight.

DRAWINGS

The drawings are SEM micrographs of hair treated ten times with compositions 9 and 16. See Example 5.

CATIONIC POLYMERS

The polymers of the invention contain one or more of the structural units depicted in structure I:

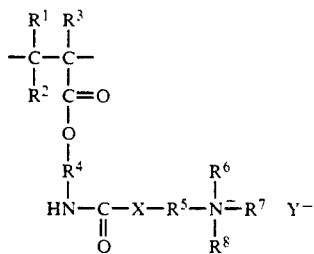

wherein:
(a) $R^1$, $R^2$ and $R^3$, are each independently selected from the group consisting of H, $NH_2$, OH, halogen, alkyl, $C_{1-6}$ alkoxy, $C_{1-6}$ aminoalkyl, $C_{1-6}$ haloalkyl, phenyl, $C_{1-6}$ alkylphenyl, $C_{1-6}$ alkoxy-phenyl, halophenyl containing 1 to 5 halogen atoms, and aminophenyl containing 1 to 5 amino groups;
(b) $R^4$ and $R^5$ are each independently alkylene units bearing from 0 to about 10 amino, halogen, hydroxy, or $C_{1-6}$ alkoxy substituents;
(c) X is —O— or —NH—;
(d) $R^6$, $R^7$, and $R^8$ are each independently $C_{1-20}$ alkyl; and
(e) Y is a halide ion or an $C_{1-6}$ alkyl sulfate ion. Thus, the polymers will have molecules which, when homopolymers, resemble formulas II and III:

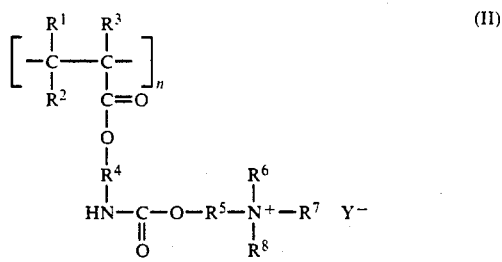

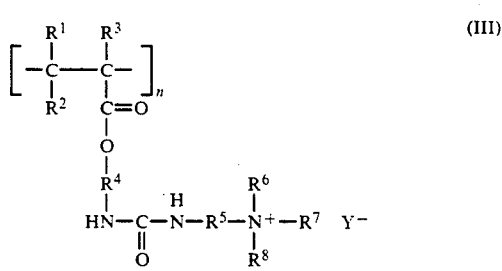

wherein n may be from about 10 to about $10^4$ (ie., 10,000), preferably about 100 to about 1,000, and the other definitions given for formula (I) apply.

It is preferred that, in structures II and III, $R^1$ and $R^2$ be H, $R^3$ be H or $CH_3$, $R^4$ and $R^5$ both be $CH_2CH_2$, $R^6$ and $R^7$ be $CH_3$ and $R^8$ be $C_{1-15}$ alkyl. It is highly preferred that $R^3$ be $CH_3$ while Y is $CH_3SO_4$ or halide ion. $Cl^-$, $Br^-$ and $I^-$ are preferred halide ions, $Br^-$ is highly preferred.

In copolymers, one group of preferred cationic molecules will contain structures of formulas IV or V:

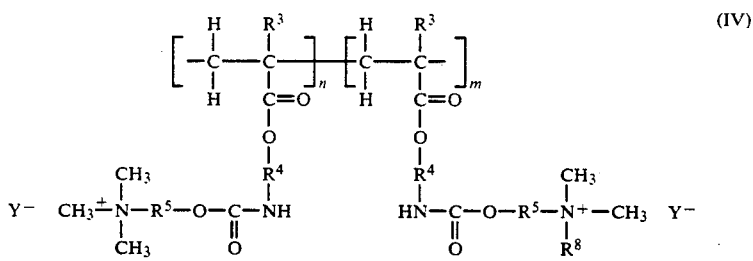

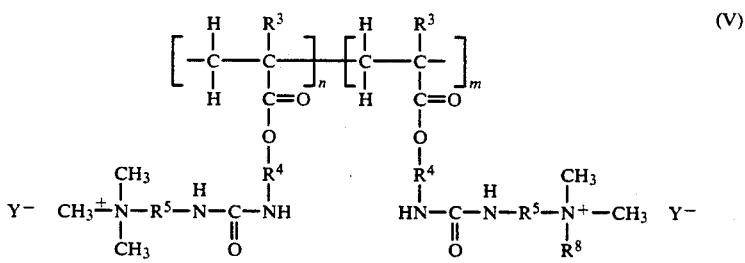

wherein the sum of $n+m$ is about 10 to $10^4$, and preferably about 100 to about 1,000; and the Y is as defined above, with Y being the same or different for each of structure (IV) and (V).

It is highly preferred that, in IV and V, $R^3$ is $CH_3$, $R^4$ and $R^5$ are $CH_2CH_2$, $R^8$ is $C_{16}H_{33}$ and Y is Br or Cl, most preferably Br.

Cationic polymers, such as poly(methacrylamidopropyltrimethyl ammonium chloride), poly(ethylmethacrylatetrimethyl ammonium halide), poly (1,1-dimethylpiperidinium-3,5-diallyl methylene chloride), and others conventionally used in the art, possess different polymer-surfactant binding characteristics than the polymers described in this invention. Acrylate, methacrylate, and dialkyldially ammonium polymers were previously described in U.S. Pat. Nos. 4,240,450, 4,150,115, 4,416,297, 4,027,008 and 3,980,769.

The cationic polymers of the invention have molecular weights in the range of about $10^3$ to about $10^6$. They are colorless in aqueous solution. They have excellent solubility in water, as well as in water-alcohol mixtures.

POLYMER PREPARATION

The polymers of the invention are prepared by the vinyl polymerization of one or more unsaturated urea- or urethane-containing monomer(s) with itself or with one or more other monomer(s).

By "vinyl polymerization", applicants mean the addition or non-condensation type of polymerization which involves free radical or similar mechanisms. There are no condensation by-products, e.g. water of condensation, produced during applicants' polymerization step.

The urea- and urethane-containing monomers are produced by the reaction of isocyanates with hydroxyl- and amine-containing reactants, respectively.

Typical reaction schemes for the production of homopolymers are set out below.

Urethane- and urea-containing homopolymers were prepared according to the following procedure starting with isocyanatoethylmethacrylate:

(a) URETHANE CONTAINING POLYMERS:

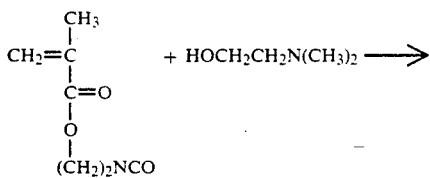

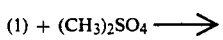

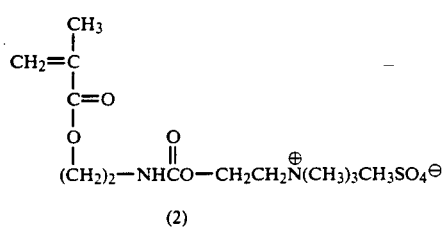

(2)

Polymerization of (2) in water ⟶

(as 40% solution)

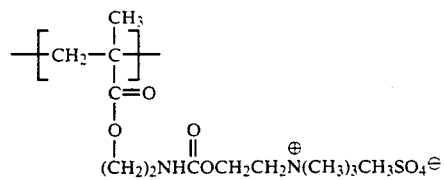

(b) UREA CONTAINING POLYMERS:

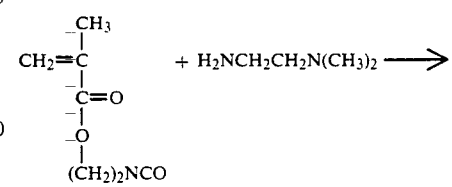

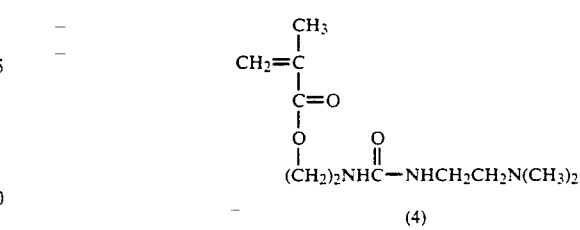

(4)

(4) + $(CH_3)_2SO_4$ ⟶

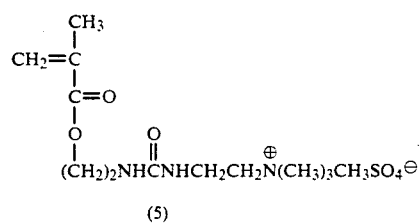

(5)

Polymerization of (5) in water ⟶

(as 40% solution)

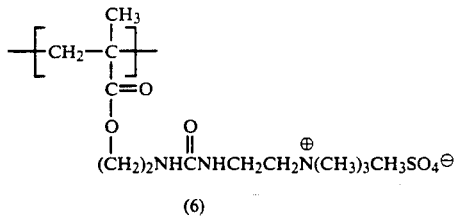

(6)

It is preferred that as soon as the urea- and urethane containing monomers are made, they be dissolved in water for reaction or preservation.

Catalysts and reagents employed in sequence (a) were dibutyltin dilaureate in preparation of (1) and potassium persulfate in the preparation of (3). Likewise, these agents or art-recognized equivalents can be used in sequence (b).

Hydrophobically modified cationic polymers, (9) and (10) above, were prepared by copolymerization of (2) and (4) with their surfactant analogs 7 and 8, (10% by mole).

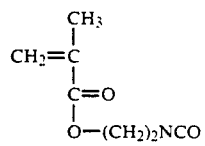 + HOCH$_2$CH$_2$N(CH$_3$)$_2$ ⟶

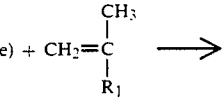 (10% by mole) + 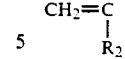 ⟶

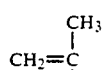

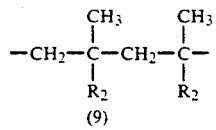

(1)

(1) + CH$_3$(CH$_2$)$_{14}$CH$_2$Br ⟶

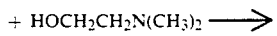 (10% by mole) + 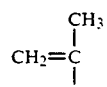 ⟶

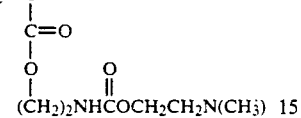

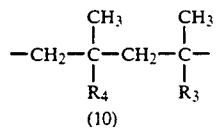

(7)

 + H$_2$NCH$_2$CH$_2$N(CH$_3$)$_2$ ⟶ 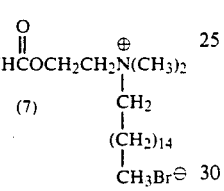

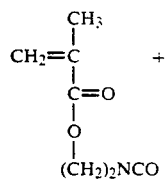

(4)

$R_1 =$ 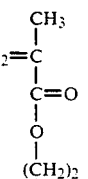 CH$_3$SO$_4^{\ominus}$    $R_2 =$ 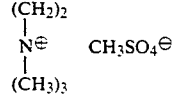 Br$^{\ominus}$ (3) + CH$_3$(CH$_2$)$_{14}$CH$_2$Br ⟶ 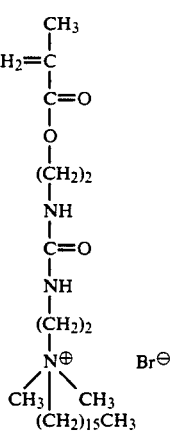

$R_3 =$ 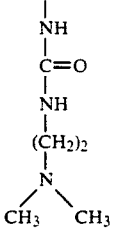 CH$_3$SO$_4^{\ominus}$    $R_4 =$ 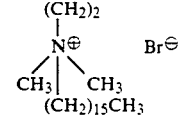 Br$^{\ominus}$ (8)

While the discussion above has centered on the urea- and urethane containing monomers, it should be noted that other addition-polymerizable or vinyl-type monomers, i.e., comonomers, can be used in making copolymers based on applicants' monomers.

Suitable comonomers, include, but are not limited to, vinyl, acetylenic and dienic monomers having various substituents. Hydrocarbon comonomers include C$_{2-10}$ compounds containing 1 or 2 unsaturated sites. Thus, ethylene, propylene, butylene etc. are operable. In addition styrene-based and, allyl and diene compounds, e.g., vinyl benzene, allyl chloride and 1,4-butadiene are also contemplated. Mixtures are operable.

Other compounds can also be copolymerized with applicants' monomers. They include $C_{2-10}$ unsaturated acids, esters, halides, amides, metal salts, preferably alkali metal or alkaline earth metal salts, ethers, anhydrides, alcoholates, and the like. Thus, vinyl halides, vinyl esters, (meth)acrylic acid, its $C_{1-10}$ esters, halides salts and amides can be used. Vinyl pyrrolidone and other heterocyclic reactants are contemplated. Mixtures are operable.

Applicants employ the term "(meth) acrylic" to refer to both C=CH—C(O)— (acrylic) and C=C(CH$_3$)—C(O)— (methacrylic) types of moieties.

When copolymers are used, it is important that, on average, at least about 70%, preferably about 50% to about 80%, of the final polymeric molecules contain the urea- or urethane-containing monomers of the invention.

It is highly preferred that hair shampoos and conditioners employ methacrylic homopolymers and copolymers containing about 80% or more of units of structure I. Minor proportions of other monomers, e.g., 5 to 50% vinyl pyrrolidone, to enhance such properties as water solubility and solution clarity may be used.

The various steps in the preparation of the polymers of the invention involve reaction techniques and devices which are conventional in the art. The temperatures at which the polymerizations occur vary from about 70° to about 80° C.

The recovery of the polymers can be effected via rinsing with conventional solvent, filtration, phase separation and the like.

COMPOSITIONS

The compositions of the invention will contain varying amounts of the electrolytic polymers and copolymers of the invention. Generally, when hair or other fibrous substrate is to be treated, the polymers will be present at concentrations of about 0.10 to about 2.0 wt. %, preferably about 0.25 to about 1.25 wt. %.

In formulations to be used to treat other keratinaceous substrates, concentrations varying from about 0.01 to about 10 wt. %, preferably about 0.75 to about 2 wt. %, are useful.

It is preferred that the cationic polymers of the invention be the only polymeric electrolytic species in the final formulations. Thus, if surfactants or other agents of polar or ionic character are included, they are preferably not polymeric in nature. If however, the use of a polymeric additive is mandated, its concentration should be kept to a minimum, ie., less than 5 wt. % of the total formulation.

The compositions of the invention may contain one or more added surfactants (ie., surface active agents) which are of nonionic, amphoteric, zwitterionic, anionic or cationic character. Generally, however only anionic and/or amphoteric ones will be found in preferred formulations.

ANIONIC SURFACTANTS

The anionic surfactants may be any of a wide variety of well-known substances. Mixtures are operable.

Preferred anionic surfactants are sodium lauryl ether sulfate (SLES), sodium lauryl sulfate (SLS), and the like.

As was stated earlier, it is preferred that the anionic surfactant not be polymeric.

It is contemplated, however, that there may be some interaction between the non-polymeric anionic surfactant and the cationic polymer of the invention. While not wanting to be bound to a particular theory, applicants believe that a complex- or salt-forming reaction or interaction, is effected which contributes to the compatibility of the anionic and cationic components, and as a result, the efficiency and stability of the formulations.

Anionic surfactants will generally be present at concentrations of about 0 to about 30 wt. %, preferably about 3 to about 15 wt. %. Mixtures can be used.

In general, the wt. ratio of anionic surfactant(s) to cationic polymer(s) in the final composition will be from about 100: 1 to about 3:1.

AMPHOTERIC SURFACTANTS

By "amphoteric surfactant," applicants mean a surfactant containing both acidic or negatively charged groups and basic, or positively charged groups. Thus, a variety of materials are useful, as are combinations of amphoterics with pH modifiers or buffers.

Useful amphoteric surfactants are well-known materials. Among them are carboxybetaines, sulfobetaines, amino acid type amphoterics and the like. Mixtures can be used.

Preferred amphoteric surfactants are alkylbetaines and alkyl amphocarboxy-propionates and the like.

As was stated in discussing anionics, it is preferred that any amphoteric surfactant used be non-polymeric.

Buffers and pH modifiers, e.g., alkalinizers or acidifiers, which are conventionally employed with amphoterics maybe included, in suitable quantities, in the formulations of the invention. The chemical nature and amounts of these additives vary widely, so long as their presence does not interfere with the function of the major components of the compositions. Concentrations of about 5 wt. % or less are conventional for amphoterics.

Since pH determines the ionic character of any amphoteric ingredient(s), it is preferred that pH's in the range of about 6 to about 9 be used when, eg., anionics with alkylamphocarboxypropionates are present and pH's of about 4 to about 9 be used when, eg., betaines with anionic surfactants are used.

Amphoteric surfactants will be present at concentrations of about 0 to about 30 wt. %., preferably about 3 to about 15 wt. %. Mixtures are contemplated.

In general, the ratio of amphoteric surfactant to cationic polymer in the final formulation will from about 100: 1 to about 3:1.

OTHER INGREDIENTS

The compositions of the invention will contain suitable quantities of a variety of ingredients conventionally used in the art. Thus, diluents, solvents, emulsifiers, stabilizers (or preservatives), plasticizers, crosslinkers, colorants, hair dyes, relaxers, perfumes, oxidants, reductants, bleaches, thickeners, etc. may be employed. The amounts used of any of these will depend upon such factors as its function, the desired properties of the final mix and the compatibility of the combinations which result.

Diluents employed will usually be one or more of water and water-miscible solvents or solvent assistants. Other useful diluents include ethanol, propanol, glycols, and the like. Stabilizers to be used in the instant formulations are generally art-recognized materials. Useful ones are methylparaben, DMDM hydantoin and the like. Mixtures may be used.

The quantity of stabilizer(s) used is not usually critical. Generally, the total stabilizer content will be an amount ranging from about 0.05 to about 0.5 wt. %.

Another useful group of ingredients in the case of shampoos are foam boosters, such as lauramide DEA. Generally, such agents will be present at concentrations of about 0.5 to about 10, preferably about 1 to about 4 wt. %.

The formulations of the invention are preferably used in the liquid state and are applied via spraying, dabbing, painting, dipping, pouring, etc. They may, however, be semi-solid or solid in character so that they are useful in paste, creams, gels, powders, or other suitable forms.

SUBSTRATES

The substrates to be treated with the formulations of the invention are generally keratinaceous or proteinaceous in character. However, non-keratinaceous and non-proteinaceous polymeric substrates, such as polyolefin fibers or strands, may also be treated.

The preferred substrates are living ones, ie., the skin and hair of live mammals, preferably human beings. However, "dead" tissue, ie., nails, wigs, and furs can also be treated.

EXAMPLES

The following examples will serve to illustrate various aspects of the invention.

Examples 1 and 2 described the preparation of the cationic urethane methacrylate polymer (polymer(3)) and urea methacrylate polymer (polymer (6)), which were produced via sequences (a) and (b), respectively. See "Polymer Preparation", supra.

EXAMPLE 1

Preparation of Cationic Urethane Methacrylate and its Polymerization (Sequence (a))

0.1 mole of isocyanathoethylmethacrylate (14.52 g) in 50 ml of dry tetrahydrofuran (THF) was added dropwise at room temperature to 0.1 mole of N,N-dimethylethanolamine (8.82 g) and one drop of dibutyltin dilaureate (0.05 % mol) in 50 ml of dry THF in a 500 ml three-necked round bottom flask. Prior to usage, the flask was dried for 24 hours at 125 C and cooled by flushing with dr nitrogen. The addition lasted about 2 hours in nitrogen atmosphere with vigorous stirring. The reaction was allowed to continue for an additional 2 hours. IR analysis wa done in order to check the disappearance of the NCO band at 2270 cml IH NMR was also done for the dried sample in CDC13, confirming the structure of the product.

0.1 mole (12.61 g plus 0.05 weight % excess = 13.24 g) of dimethylsulfate in 25 ml of dry THF was added dropwise to the reaction product at room temperature. Care was taken to avoid the temperature rise. The addition lasted about 2 hours. Separation of the quaternized product was observed. Analysis of the product was done by $^1$H NMR in CDCl$_3$ to confirm complete quaternization. The reaction mixture was immediately refrigerated in order to avoid the polymerization.

The THF solvent was decanted and 10 g of the monomer was dissolved in 20 ml of distilled water along with 0.25% by weight of potassium persulfate (25 mg) and polymerized at 60.C. This polymer is Polymer (3).

EXAMPLE 2

Preparation of Cationic Urea Methacrylate and its Polymerization 0.1 mole of isocyanatoethylmethacrylate (14.52 g) in 50 ml of dry THF was added dropwise at room temperature to 0.1 mole of N,N-dimethylethylenediamine (8.82 g) in 50 ml of dry THF in a 500 ml three-necked round bottom flask (no catalyst). Prior to usage, the flask was dried for 24 hours at 125° C. and cooled by flushing with dry nitrogen. The addition lasted about 2 hours in nitrogen atmosphere with vigorous stirring. The reaction was allowed to continue for an additional 2 hours. IR analysis was done in order to check the disappearance of NCO band at 2270 cm$^1$ $^1$H NMR was also done for the dried sample in CDCl$_3$ confirming the structure of the product.

0.1 mole (12.61 g plus 0.05 weight % excess = 13.24 g) of dimethylsulfate in 25 ml of dry THF was added drop-wise to the reaction mixture at room temperature. Care was taken to avoid a temperature increase. The addition lasted about 2 hours. Separation of the quaternized product was observed. Analysis of the product was done by $^1$H NMR in CDCl$_3$ to confirm complete quaternization. The product was immediately refrigerated in order to avoid the polymerization.

The solvent (THF) was decanted and 10 g of the monomer was dissolved in 20 ml of distilled water along with 0.25% by weight of potassium persulfate (25 mg) and polymerized at 60° C. This is Polymer (6).

EXAMPLE 3

Evaluation of Polymers (3) and (6) as conditioners

1% aqueous solutions of polymers (3) and (6), which were prepared according to Examples 1 and 2, were tested as conditioning lotions on untreated hair and rated on the scale from 0 (very difficult combing) to 5 (very easy combing). The scores were 2.0 and 3.5 for lotions with urethane-and urea-containing polymers, respectively.

EXAMPLE 4

Formulations containing Cationic Polymers with Anionic-Amphoteric Surfactant System (Compositions 1-4) and Amphoteric Surfactant Alone (Compositions 5-7).

The following compositions were tested as shampoos using a standard procedure. That procedure involved wetting a 2 g hair tress, applying approximately 1g of a formulation, washing the shampoo into the hair forming a lather for 1 minutes, during which time the hair was combed through 10 times, using the narrow toothed section of a hand comb. The hair tress was then rinsed for 30 seconds under 30-35° C. tap water (flow rate 2 liters/min) before the evaluation of combing ease.

Examples of formulations:

| Shampoo compositions containing anionic-amphoteric surfactant system | |
|---|---|
| Composition 1 | |
| Cocobetaine (44% active) | 30.0 g |
| SLES (25% active) | 30.0 g |
| Polymer 3 (20% active) | 7.5 g |
| Lauramide DEA | 1.5 g |
| Methyl paraben | 0.15 g |
| DMDM hydantoin | 0.45 g |
| D. I. Water | 77.4 g |

Shampoo compositions containing anionic-amphoteric surfactant system

Composition 2

| | |
|---|---|
| Cocobetaine (44% active) | 30.0 g |
| SLES (25% active) | 30.0 g |
| Polymer 6 (25% active) | 6.0 g |
| Lauramide DEA | 6.0 g |
| Methyl paraben | 0.15 g |
| DMDM hydantoin | 0.45 g |
| D. I. Water | 77.4 g |

Composition 3

| | |
|---|---|
| Cocobetaine (44% active) | 30.0 g |
| SLES (25% active) | 36.0 g |
| Polymer 10 (20% active) | 3.75 g |
| Lauramide DEA | 3.0 g |
| Methyl paraben | 0.15 g |
| DMDM hydantoin | 0.45 g |
| D. I. Water | 76.65 g |

Composition 4

| | |
|---|---|
| Cocoamphocarboxypropionate (39%) | 90.0 g |
| SLES (25% active) | 60.0 g |
| PEG-6000 disterate | 2.25 g |
| Polymer 3 (20% active) | 22.5 g |
| Methyl paraben | 0.3 g |
| D. I. Water | 124.95 g |

All these compositions, used as shampoos, significantly improve the combability of untreated hair. Combability was rated as stated in Example 3.

Shampoo compositions containing amphoteric surfactant

Composition 5

| | |
|---|---|
| Cocoamphocarboxypropionate (39% active) | 120.0 g |
| Polymer 6 (25% active) | 18.0 g |
| PEG-6000 disterate | 2.25 g |
| DMDM hydantoin | 0.6 g |
| Methyl paraben | 03 g |
| D. I. Water | 158.85 g |

Composition 6

| | |
|---|---|
| Cocoamphocarboxypropionate (39% active) | 120.0 g |
| Polymer 3 II (20% active) | 22.5 g |
| PEG-6000 disterate | 2.25 g |
| Methyl paraben | 0.3 g |
| D. I. Water | 154.95 g |

Composition 7

| | |
|---|---|
| Cocoamphocarboxypropionate (39% active) | 60.0 g |
| Polymer 10 (20% active) | 9.0 g |
| PEG-6000 distearate | 1.125 g |
| Methyl paraben | 0.15 g |
| D. I. Water | 79.725 g |

Compositions 5-7, used as shampoos, significantly improve wet combability of untreated hair.

EXAMPLE 5 Various Shampoos

Shampoo compositions based on urea-containing polymer (6) (similar to composition 2) were studied in a systematic manner by varying the concentration of the polymer and lauramide DEA. The results are presented in the following Table and compared with the systems comprising hydrophobically modified urethane containing polymer (10), poly (methacrylateethyltrimethyl ammonium methyl sulfate), poly(methacrylamidopropyltrimethyl) ammonium chloride), commercially available compositions Pert Plus (manufactured by Procter and Gamble) and Milk Plus Six (manufactured by Revlon Inc.) and a control system without a polymer.

TABLE

Conditioning Shampoo Compositions Based on Cocobetaine-Sodium Lauryl Ether Sulfate (SLES)

| Cmpn. No. | Cocobetaine (44% act) % | SLES (25% act) % | Polymer % | LDEA (100% act) % | Viscosity (CPS) | Combability* | Foaming (ml)** | Remarks (ml) |
|---|---|---|---|---|---|---|---|---|
| Surfactant System | | | | | | | | |
| 8 | 20 | 20 | 6.0 | — | 760 | 4–5 | 105 | pH 7–8 |
| 9 | 20 | 20 | 5.0 | 4.0 | 475 | 4 | 135 | No coating acc. to SEM |
| 10 | 20 | 20 | 4.0 | 4.0 | 510 | 3.5 | 125 | — |
| 11 | 20 | 20 | 2.0 | 4.0 | 360 | 1–2 | 135 | No coating acc. to SEM |
| 12 | 20 | 20 | 1.0 | 4.0 | 260 | 1 | 150 | — |
| 13 | 20 | 20 | 0.4 | 1.0 | 4700 | 0.5 | 155 | — |
| 14 | 20 | 20 | 5.0 | 2.0 | 3150 | 4 | 125 | — |
| 15 | 10 | 30 | 1.0 | 1.0 | 9700 | 0.5–1 | 130 | — |
| System with Hydrophobically Modified Urethane-containing Polymer (g) (20% active). | | | | | | | | |
| 16 | 20 | 20 | 5.0 | 1.0 | — | 3–4 | 150 | |
| Control System without Polymer | | | | | | | | |
| 17 | 20 | 20 | 0.0 | 4.0 | 200 | 0 | 165 | |
| System with Poly (methacrylamido propyltrimethyl ammonium chloride) | | | | | | | | |
| 18 | 20 | 20 | 4.5 | 0.0 | | | | |
| System with Poly (trimethylethylmethacrylate Ammonium Methylsulfate) (20% Active) | | | | | | | | |
| 19 | 20 | 20 | 5.0 | 2.0 | — | — | | Precipitation of the complex |
| Pert Plus | | | | | | | | |
| 20 | — | — | — | — | — | 0.5 | 180 | — |
| Milk +6 | | | | | | | | |
| 21 | — | — | — | — | — | 4.0 | — | No coating acc. to SEM |

*Combability scale was 0–5, with 0 being an untreated control (difficult to comb) and 5 being the combability using a standard conditioner (easily combed).
**Height of foam produced by tumbling 1 g. of shampoo and 50 ml. of water, 20 times inside a 250 ml. graduated cylinder.

RESULTS OF EXAMPLES 1-4

All compositions with urea and urethane-containing polymers (homopolymers or copolymers) produce perceptible improvements in wet combability. The extent of this effect (Table I, column 7), appears to be determined by the concentration of a polymer in the formulation.

For urea containing polymers, the polymer concentration range of practical importance appears to be from 0.25% to 1.25%. At 0.25%, the conditioning effect becomes detectable, although it is very small. At 1.25%, the conditioning effect is clearly evident and the formulation is not coating hair excessively even after multiple shampooings.

The use of other cationic polymers such as poly-(methacrylamidopropyltrimethylammonium chloride) and poly (trimethylethylmethacrylate ammonium methylsulfate) led to nonhomogeneous compositions which precipitated complex particles.

Foaming seems to be dependent upon polymer concentration with less foam formed at high concentration of the polymer (compare compositions 17 and 8-13).

The viscosity of the formulations appears to be inversely proportional to the concentration of lauramide DEA (LDEA) (compare compositions 9 and 14) It is also weakly dependent upon the concentration of the polymer, with higher viscosities obtained at higher polymer concentrations (compare compositions 9-12).

RESULTS OF EXAMPLE 5

Examinations were made of multiply shampooed hair using a Scanning Election Microscope (SEM).

Figure 2:
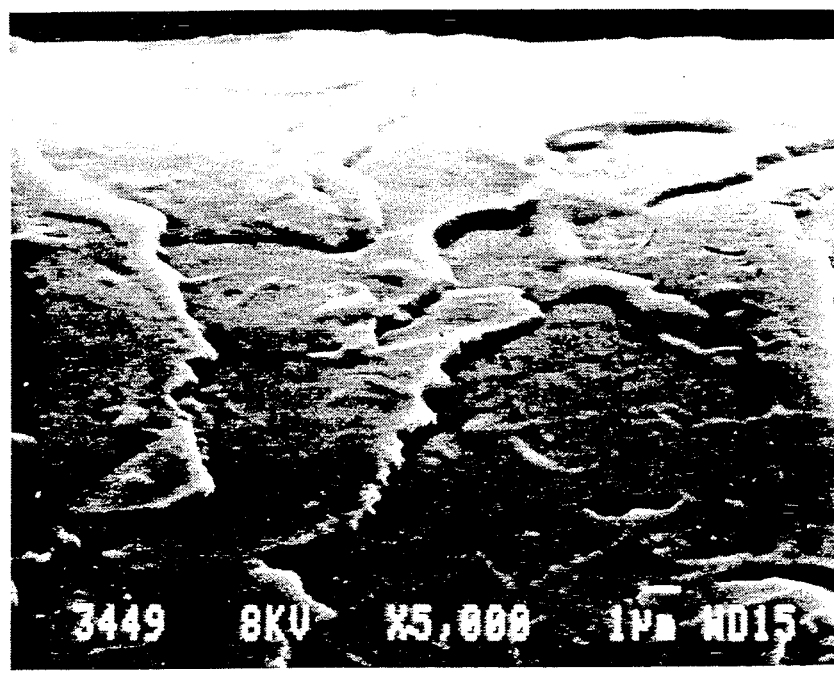

Samples of hair after multiple (8-10) shampooings, with and without drying between shampooings with formulations 9 and 11 showed no surface deposits of polymer-surfactant complex. A typical SEM micrograph of the hair surface after 10 consecutive shampooings (without drying in between shampooings) is shown in FIG. 1. In the case of one hair tress shampooed 10 times with formulation 16 (with drying in between shampooings), SEM analysis showed the accumulation of the complex on the surface of hair (FIG. 2). However, repetition of this experiment on a different hair tress did not show any surface deposits.

Also ten (10) shampooings without drying hair between shampooings did not produce any evidence of excessive coating of hair after treatment with this composition. In addition to this, small panel tests showed that hair tresses treated with compositions 9, 11, and 16, cannot be distinguished from untreated controls.

Reasonable variations, such as those which would occur to a skilled artisan, can be made herein without departing from the scope of the invention.

We claim:

1. A composition for treating keratinaceous substrates which contains a cationic polymer comprising units of formula I:

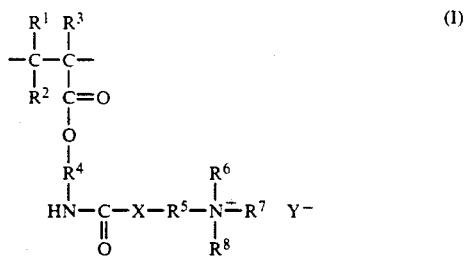

wherein:
(a) $R^1$, $R^2$ and $R^3$ are each independently selected from the group consisting of H, halogen, alkyl, $C_{1-6}$ alkoxy, $C_{1-6}$ aminoalkyl, $C_{1-6}$ haloalkyl, phenyl, $C_{1-6}$ alkylphenyl, $C_{1-6}$ alkoxyphenyl, halophenyl containing 1 to 5 halogen atoms, and aminophenyl containing 1 to 5 amino groups;
(b) $R^4$ and $R^5$ are each independently $C_{1-20}$ alkylene linkages bearing from 0 to 10 halogen or $C_{1-6}$ alkoxy substituents;
(e) Y is a halide ion or $C_{1-6}$ alkyl sulfate ion;
in the presence of a non-polymeric surfactant selected from the group consisting of amphoteric surfactants, anionic surfactants and mixtures thereof.

2. The composition of claim 1 wherein
$R^1$ and $R^2$ are H;
$R^3$ is selected from H and $CH_3$; and
$R^4$ and $R^5$ are $CH_2CH_2$ groups.

3. The composition of claim 2 wherein
$R^6$ and $R^7$ are $CH_3$; and
Y is selected from $Br^-$ and $CH_3SO_4-$ 4. A process for treating a keratinaceous substrate comprising the step of contacting the substrate with the composition of claim 1.

5. A process for treating a keratinaceous substrate comprising the step of contacting the substrate with the composition of claim 2.

6. A process for treating a keratinaceous substrate comprising the step of contacting the substrate with the composition of claim 3.

* * * * *